United States Patent [19]

Cupps et al.

[11] Patent Number: 5,541,210

[45] Date of Patent: Jul. 30, 1996

[54] 5-(2-IMIDAZOLINYLAMINO) BENZIMIDAZOLE COMPOUNDS USEFUL AS ALPHA-2 ANDRENOCEPTOR AGONISTS

[75] Inventors: Thomas L. Cupps, Oxford; Sophie E. Bogdan, Maineville, both of Ohio

[73] Assignee: The Procter & Gamble Company, Cincinnati, Ohio

[21] Appl. No.: 496,706

[22] Filed: Jun. 29, 1995

Related U.S. Application Data

[63] Continuation-in-part of Ser. No. 349,558, Dec. 8, 1994, Pat. No. 5,478,858, which is a continuation-in-part of Ser. No. 169,868, Dec. 17, 1993, abandoned.

[51] Int. Cl.$^6$ ................................................ A61K 31/415
[52] U.S. Cl. .................................................................. 514/394
[58] Field of Search ............................................... 514/394

[56] References Cited

U.S. PATENT DOCUMENTS

| | | | |
|---|---|---|---|
| 3,890,319 | 6/1975 | Danielewicz et al. | 260/250 |
| 4,029,792 | 6/1977 | Danielewicz et al. | 424/251 |
| 4,036,976 | 7/1977 | Neumann | 424/273 |
| 4,217,356 | 8/1980 | Neumann | 424/270 |
| 4,398,028 | 8/1983 | Neumann | 544/331 |
| 5,021,416 | 6/1991 | Gluchowski | 514/249 |
| 5,091,528 | 2/1992 | Gluchowski | 544/105 |
| 5,180,721 | 1/1993 | Burke | 514/213 |
| 5,231,096 | 7/1993 | Gluchowski et al. | 514/249 |
| 5,281,591 | 1/1994 | Burke | 514/213 |

FOREIGN PATENT DOCUMENTS

| | | | |
|---|---|---|---|
| 0047328 | 3/1982 | European Pat. Off. | C07D 403/12 |
| 0025269 | 3/1991 | European Pat. Off. | A61K 31/155 |
| 2638356 | 4/1990 | France | A61K 31/415 |
| 92/21349 | 12/1992 | WIPO | A61K 31/55 |

OTHER PUBLICATIONS

Cambridge, D., "UK–14,304, A Potent and Selective $\alpha_2$–Agonist for the Characterization of $\alpha$–Adrenoceptor Subtypes", *European Journal of Pharmacology*, vol. 72, pp. 413–415 (no month identified 1981).

Chapleo, C. B., J. C. Doxey, P. L. Myers, M. Myers, C. F. C. Smith and M. R. Stillings, "Effect of 1,4–Dioxanyl Substitution on the Adrenergic Activity of Some Standard $\alpha$–Adrenoreceptor Agents", *European Journal of Medicinal Chemistry*, vol. 24, pp. 619–622 (no month identified 1989).

Chapleo, C. B., R. C. M. Butler, D. C. England, P. L. Myers, A. G. Roach, C. F. C. Smith, M. R. Stillings and I. F. Tulloch, "Heteroaromatic Analogues of the $\alpha_2$–Adrenoreceptor Partial Agonist Clondine", *J. Med. Chem.*, vol. 32, pp. 1627–1630 (no month identified 1989).

Clare, K. A., M. C. Scrutton and N. T. Thompson, "Effects of $\alpha_2$–Adrenoreceptor Agonists and of Related Compounds on Aggregation of, and on Adenylate Cyclose Activity in, Human Platelets", *Br. J. Pharmacl*, vol. 82, pp. 467–476 (no month identified 1984).

Megens, A. A. H. P., J. E. Leysen, F. H. L. Awouters and C. J. E. Niemegeers, "Ruther Validation of In Vivo and In Vitro Pharmacological Procedures for Assessing the $\alpha_2/\alpha_1$–Selectivity of Test Compounds: (2) $\alpha$–Adrenoceptor Agonists", *European Journal of Pharmacology*, vol. 129, pp. 57–64 (no month identified 1986).

Timmermans, P. B. M. W. M. and P. A. van Zwieten, "$\alpha_2$–Adrenoceptor Agonists and Antagonists", *Drugs of the Future*, vol., 9, No. 1, pp. 41–55 (Jan., 1984).

Timmermans, P. B. M. W. M. A. T. Chiu and M. J. M. C. Thoolen, "12,1 $\alpha_2$–Adrenergic Receptors", *Comprehensive Medicinal Chemistry*, vol. 3, Membranes & Receptors, pp. 133–185 (no month identified 1990).

Timmermans, P. B. M. W. M. A. de Jonge, M. J. M. C. Thoolen, B. Wilffert, H. Batink and P. A. van Zwieten, "Quantitative Relationships between $\alpha_2$–Adrenergic Activity and Binding Affinity of $\alpha_2$–Adrenoceptor Agonists and Antagonists", *J. Med. Chem.*, vol. 27, pp. 495–503 (no month identified 1984).

Van Meel, J. C. A., A. de Jonge, P. B. M. W. M. Timmermans and P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, vol. 219, pp. 760–767 (no month identified 1981).

Zinchenko, T. M., "Investigation of Autoallergenic Action of Dibutyl and Dioctyl Phthalates", *Gig. Sanit.*, vol. 1, pp. 79–80. (1985).

*Primary Examiner*—Kimberly Jordan
*Attorney, Agent, or Firm*—Richard A. Hake; Karen F. Clark; Milton B. Graff, IV

[57] ABSTRACT

The subject invention involves compounds having the following structure:

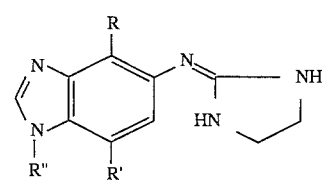

wherein:

(a) R is unsubstituted $C_1$–$C_3$ alkanyl or alkenyl;

(b) R' is selected from hydrogen; unsubstituted $C_1$–$C_3$ alkanyl or alkenyl; unsubstituted $C_1$–$C_3$ alkylthio or alkoxy; hydroxy; thiol; cyano; and halo; and (c) R' is selected from hydrogen, methyl, ethyl and i-propyl.

The subject invention also involves pharmaceutical compositions containing such novel compounds, compositions thereof and the use of such compounds for preventing or treating respiratory, ocular and/or gastrointestinal disorders.

15 Claims, No Drawings

5-(2-IMIDAZOLINYLAMINO)BENZIMIDAZOLE COMPOUNDS USEFUL AS ALPHA-2 ANDRENOCEPTOR AGONISTS

This is a continuation-in-part of application Ser. No. 08/349,558, filed on Dec. 8, 1994, now U.S. Pat. No. 5,478,858 which is a continuation-in-part of Ser. No. 08/169,868, filed on Dec. 17, 1993, now abandoned.

TECHNICAL FIELD

The subject invention relates to certain substituted 5-(2-imidazolinylamino)benzimidazole compounds. The compounds have been found to be alpha adrenoceptor agonists and are useful for treatment of one or more of respiratory disorders.

BACKGROUND OF THE INVENTION

Information regarding alpha adrenergic receptors, agonists and antagonists, in general, and regarding compounds related in structure to those of the subject invention are disclosed in the following references: Timmermans, P.B.M.W.M., A. T. Chiu & M.J.M.C. Thoolen, "12.1 α-Adrenergic Receptors", *Comprehensive Medicinal Chemistry*, Vol. 3, Membranes & Receptors, P. G. Sammes & J. B. Taylor, eds., Pergamon Press (1990), pp. 133–185; Timmermans, P.B.M.W.M. & P. A. van Zwieten," α-Adrenoceptor Agonists and Antagonists", *Drugs of the Future*, Vol. 9, No. 1, (January, 1984), pp. 41–55; Megens, A.A.H.P., J. E. Leysen, F. H. L. Awouters & C. J. E. Niemegeers, "Further Validation of in vivo and in vitro Pharmacological Procedures for Assessing the $\alpha_1$ and $\alpha_2$-Selectivity of Test Compounds: (2) α-Adrenoceptor Agonists", *European Journal of Pharmacology*, Vol. 129 (1986), pp. 57–64; Timmermans, P.B.M.W.M., A. de Jonge, M.J.M.C. Thoolen, B. Wilfred, H. Batink & P. A. van Zwieten, "Quantitative Relationships between α-Adrenergic Activity and Binding Affinity of α-Adrenoceptor Agonists and Antagonists", *Journal of Medicinal Chemistry*, Vol. 27 (1984) pp. 495–503; van Meel, J. C. A., A. de Jonge, P.B.M.W.M. Timmermans & P. A. van Zwieten, "Selectivity of Some Alpha Adrenoceptor Agonists for Peripheral Alpha-1 and Alpha-2 Adrenoceptors in the Normotensive Rat", *The Journal of Pharmacology and Experimental Therapeutics*, Vol. 219, No. 3 (1981), pp. 760–767; Chapleo, C. B., J. C. Doxey, P. L. Myers, M. Myers, C. F. C. Smith & M. R. Stillings, "Effect of 1,4-Dioxanyl Substitution on the Adrenergic Activity of Some Standard α-Adrenoreceptor Agents", *European Journal of Medicinal Chemistry*, Vol. 24 (1989), pp. 619–622; Chapleo, C. B., R. C. M. Butler, D. C. England, P. L. Myers, A. G. Roach, C. F. C. Smith, M. R. Stillings & I. F. Tulloch, "Heteroaromatic Analogues of the $\alpha_2$-Adrenoreceptor Partial Agonist Clondine", *J. Med. Chem.*, Vol. 32 (1989), pp. 1627–1630; Clare, K. A., M. C. Scrutton & N. T. Thompson, "Effects of $\alpha_2$-Adrenoceptor Agonists and of Related Compounds on Aggregation of, and on Adenylate Cyclase Activity in, Human Platelets", *Br. J. Pharmac.*, Vol. 82 (1984), pp. 467–476; U.S. Pat. No. 3,890,319 issued to Danielewicz, Snarey & Thomas on Jun. 17, 1975; and U.S. Pat. No. 5,091,528 issued to Gluchowski on Feb. 25, 1992. However, many compounds related in structure to those of the subject invention do not provide the activity and specificity desirable when treating respiratory, ocular or gastrointestinal disorders.

It is particularly relevant to the subject invention that compounds found to be effective nasal decongestants are frequently found to have undesirable side effects, such as causing hypertension and insomnia, particularly when administered systemically. There is a need for new drugs which provide relief from nasal congestion without causing these undesirable side effects.

It is an object of the subject invention to provide novel compounds having substantial activity in preventing or treating nasal congestion.

It is a further object of the subject invention to provide such compounds which do not cause hypotension, drowsiness, hypertension, insomnia or other undesirable side effects, particularly when administered systemically.

It is also an object of the subject invention to provide novel compounds for treating cough, chronic obstructive pulmonary disease (COPD) and/or asthma.

It is also an object of the subject invention to provide novel compounds for treating glaucoma and/or diarrhea.

It is a still further object of the subject invention to provide such compounds which have good activity from peroral and/or topical and/or intranasal dosing.

It is an object of the subject invention to provide such novel compounds in pharmaceutically acceptable compositions.

It is an object of the subject invention to provide such novel compounds in pharmaceutically acceptable compositions in combinations with other active which provide further theraputic benefit.

SUMMARY OF THE INVENTION

The subject invention relates compounds having the following structure:

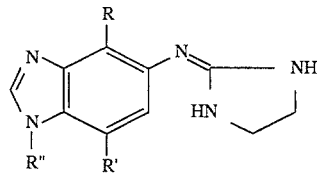

wherein:

(a) R is unsubstituted $C_1$–$C_3$ alkanyl or alkenyl;

(b) R' is selected from hydrogen; unsubstituted $C_1$–$C_3$ alkanyl or alkenyl; unsubstituted $C_1$–$C_3$ alkylthio or alkoxy; hydroxy; thiol; cyano; and halo; and (c) R" is selected from hydrogen, methyl, ethyl and i-propyl; pharmaceutical compositions containing such novel compounds, and the use of such compounds for preventing or treating other respiratory, ocular and/or gastrointestinal disorders.

DETAILED DESCRIPTION OF THE INVENTION

As used herein, "alkanyl" means a saturated hydrocarbon substituent, straight or branched chain, unsubstituted or substituted. As used herein, "alkenyl" means a hydrocarbon substituent with one double bond, straight or branched chain, unsubstituted or substituted. As used herein, "alkylthio" means a substituent having the structure Q—S—, where Q is alkanyl or alkenyl.

As used herein, "alkoxy" means a substituent having the structure Q—O—, where Q is alkanyl or alkenyl.

Compounds

The subject invention involves compounds having the following structure:

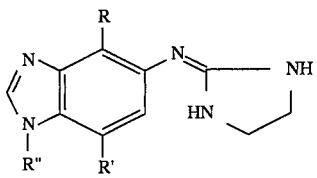

In the above structure, R is unsubstituted alkanyl or alkenyl having from 1 to about 3 carbon atoms. R is preferably alkanyl. R is most preferably methyl or ethyl.

In the above structure, R' is selected from hydrogen; unsubstituted alkanyl or alkenyl having from 1 to about 3 carbon atoms; unsubstituted alkylthio or alkoxy having from 1 to about 3 carbon atoms; hydroxy; thiol; cyano; and halo. R' is preferably hydrogen. R' is also preferably alkanyl, more preferably methyl or ethyl, most preferably methyl. R' which is alkylthio or alkoxy is preferably saturated, also preferably $C_1$ or $C_2$, more preferably methylthio or methoxy. R' which is halo is preferably chloro or bromo or fluoro, more preferably chloro or especially fluoro.

In the above structure, R" is selected from hydrogen, methyl, ethyl and i-propyl. R" is preferably hydrogen, methyl or ethyl, more preferably hydrogen or methyl, most preferably hydrogen.

Preferred compounds of the subject invention have the following structure:

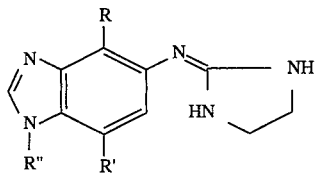

where R, R' and R" are as indicated in the following table:

| Compound No. | R | R' | R" |
|---|---|---|---|
| 1 | $CH_3$ | H | H |
| 2 | $CH_2CH_3$ | H | H |
| 3 | $CH_3$ | $CH_3$ | H |
| 4 | $CH_3$ | H | $CH_3$ |
| 5 | $CH_3$ | F | H |

The compounds of the subject invention are particularly useful for the treatment of nasal congestion associated with allergies, colds, and other nasal disorders with associated nasal congestion, as well as their sequelae (for example, sinusitis and otitis). At the same time, it has been found that undesired side effects, such as hypotension, drowsiness, hypertension, or insomnia can often be avoided. While not limited to a particular mechanism of action, the subject compounds are believed to provide advantages in the treatment of nasal decongestion over related compounds through their ability to interact with alpha-2 adrenoceptors. The subject compounds have been found to be alpha-2 adrenoceptor agonists which cause constriction of peripheral vascular beds in the turbinates.

Particular subject compounds have no or only weak alpha-1 agonist activity, and have little or no effect on the central nervous system, even when dosed systemically.

The compounds of the subject invention are also useful for the treatment of ocular disorders associated with increased intraocular pressure, such as glaucoma. The compounds are administered either perorally, or topically as drops, gels or creams directly to the surface of the mammalian eye.

The compounds of the subject invention are also useful for controlling gastrointestinal motility disorders, such as diarrhea, by antimotility and antisecretory actions on the gastrointestinal tract.

The pharmacological activity and selectivity of the subject compounds can be determined using published test procedures. The alpha-2 selectivity of the compounds is determined by measuring receptor binding affinities and in vitro functional potencies in a variety of tissues known to possess alpha-2 and/or alpha-1 receptors. (See, e.g., *The Alpha- 2 Adrenergic Receptors*, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", *J. Neural. Trans.*, Vol. 54 (1982), pp. 153–163). Nasal decongestant activity is measured using rhinomanometry as an estimate of nasal airway resistance. (See, e.g., Salem, S. & E. Clemente, "A New Experimental Method for Evaluating Drugs in the Nasal Cavity", *Arch. Otolarynng*, Vol. 96 (1972), pp. 524–529). Antiglaucoma activity is determined by measuring intraocular pressure. (See, e.g., Potter, D., "Adrenergic Pharmacology of Aqueous Human Dynamics", *Pharmacol. Rev.*, Vol. 13 (1981), pp. 133–153). Antidiarrheal activity is determined by measuring the ability of the compounds to inhibit prostaglandin-induced diarrhea. (See, e.g., Thollander, M., P. Hellstrom & T. Svensson, "Suppression of Castor Oil-Induced Diarrhea by Alpha-2 Adrenoceptor Agonists", *Aliment. Pharmacol. Therap.*, Vol. 5 (1991), pp. 255–262). Antiasthma activity is determined by measuring the effect of the compound on bronchoconstriction associated with pulmonary challenges such as inhaled antigens. (See, e.g., Chang, J. J. Musser & J. Hind, "Effects of a Novel Leukotriene $D_4$ Antagonist with 5-Lipoxygenase and Cyclooxygenase Inhibitory Activity, Wy-45,911, on Leukotriene-$D_4$- and Antigen-Induced Bronchoconstriction in Guinea Pig", *Int. Arch. Allergy Appl. Immun.*, Vol. 86 (1988), pp. 48–54; and Delehunt, J., A. Perruchound, L. Yerger, B. Marchette, J. Stevenson & W. Abraham, "The Role of Slow-Reacting Substance of Anaphylaxis in the Late Bronchial Response After Antigen Challenge in Allergic Sheep", *Am. Rev. Respir. Dis.*, Vol. 130 (1984), pp. 748–754). Activity in cough is determined by measuring the number and latency of the cough response to respiratory challenges such as inhaled citric acid. (See, e.g., Callaway, J. & R. King, "Effects of Inhaled Alpha-2-Adrenoceptor and $GABA_B$ Receptor Agonists on Citric Acid-Induced Cough and Tidal Volume Changes in Guinea Pigs", *Eur. J. Pharmacol.*, Vol. 220 (1992), pp. 187–195).

The compounds of the subject invention are synthesized using the following general procedures:

Scheme 1
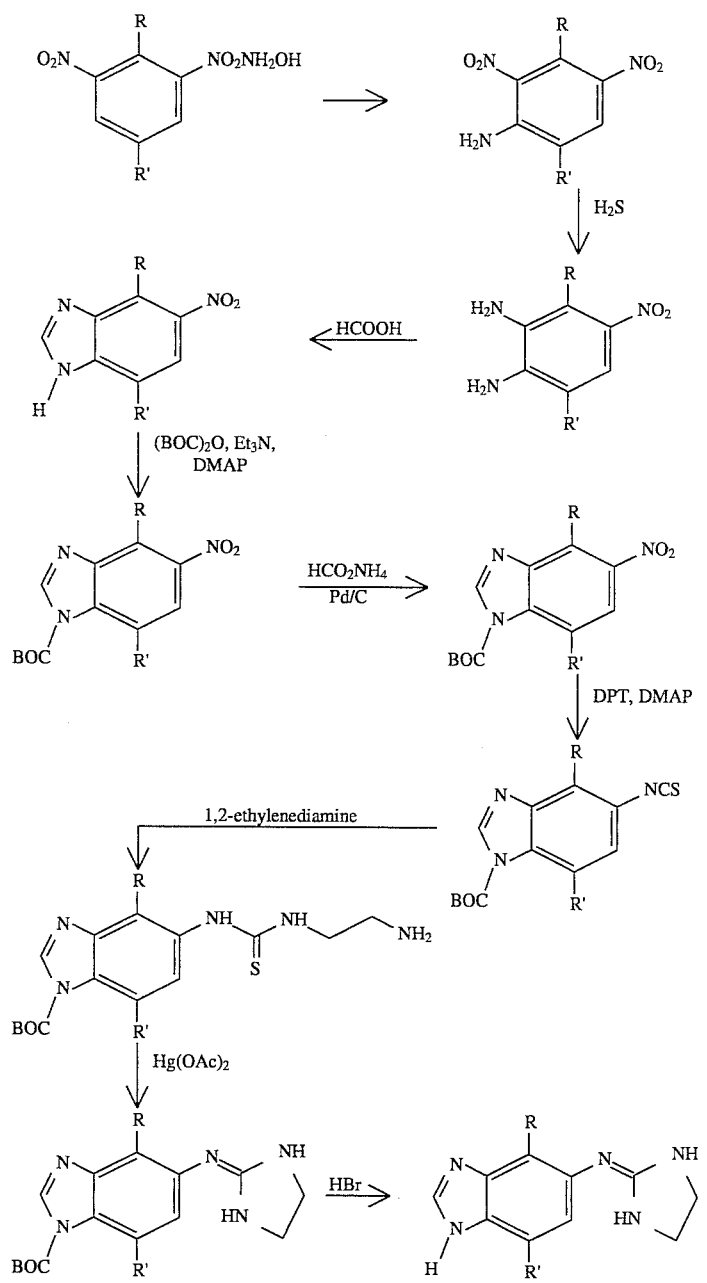
Scheme 2
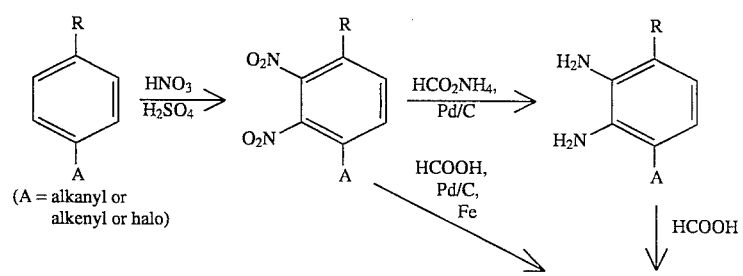

-continued
Scheme 2
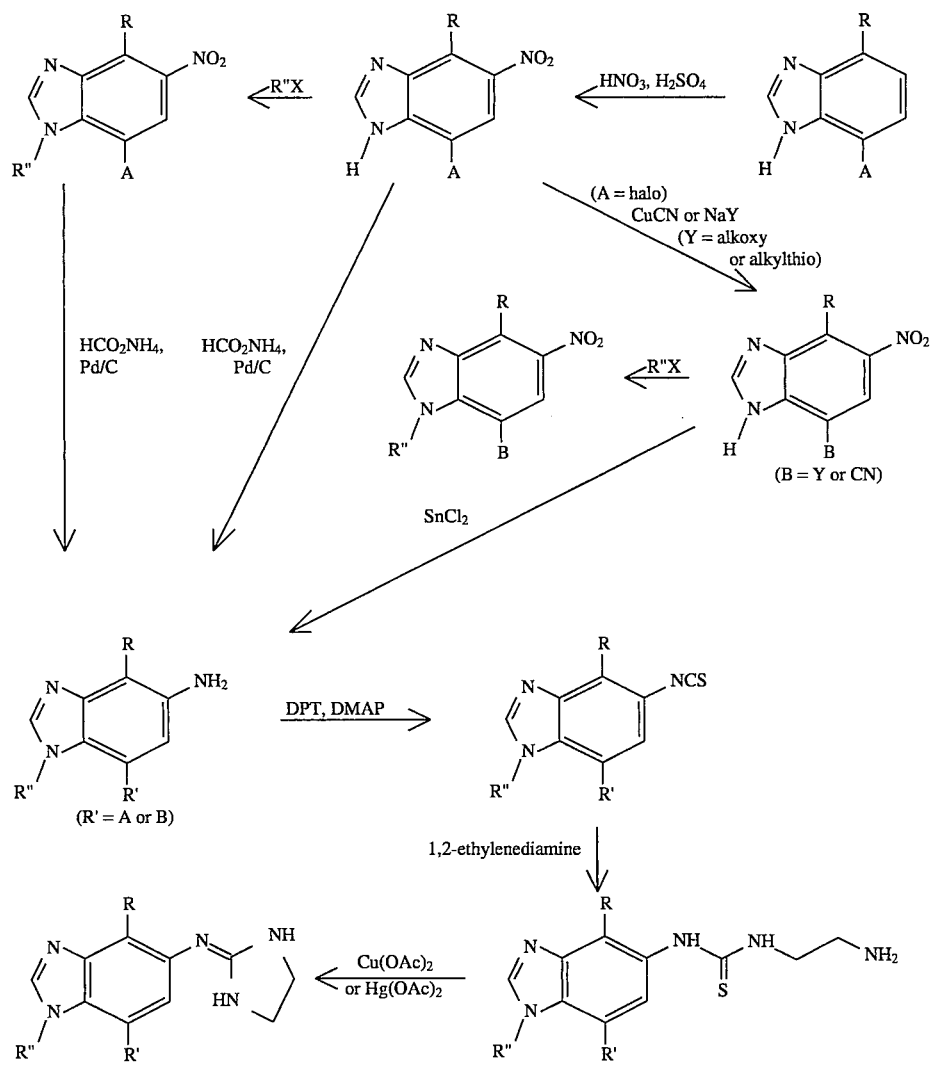
Scheme 3
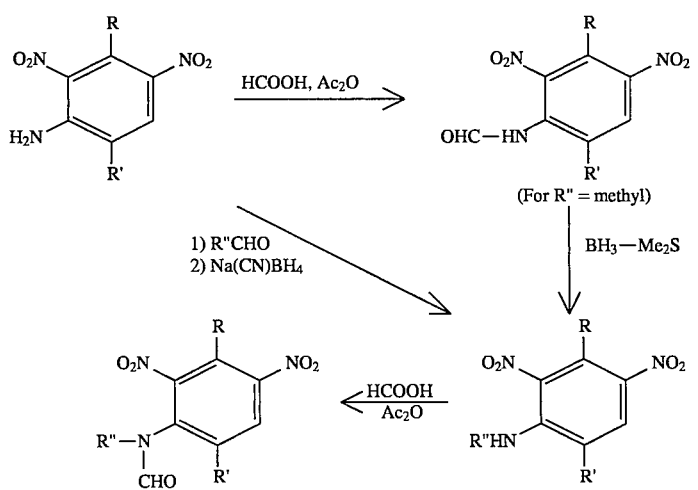

-continued
Scheme 3

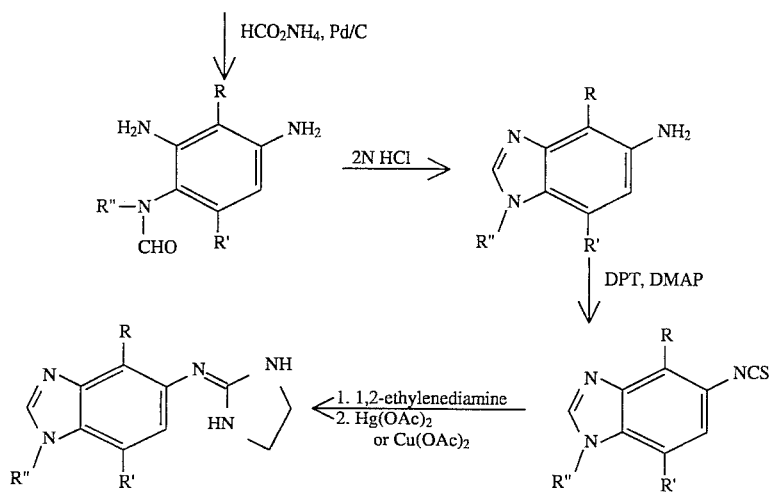

In the above schemes, where R' is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

Synthesis Examples

The following non-limiting examples provide details for the synthesis of 5-imidazolinylaminobenzimidazoles:

EXAMPLE 1

Synthesis of 4-methyl-5-(2-imidazolinylamino) benzimidazole dihydrobromide:

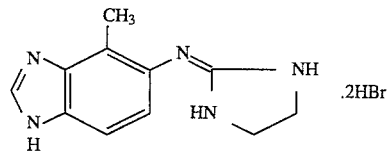

2,3-diamino-6-nitrotoluene. To a solution 3-methyl-2,4-dinitroaniline (30 g) in boiling ethanol (750 mL) is added dropwise over 90 minutes a solution of sodium sulfide nonahydrate (109.6 g) in water (750 mL). At the end of the addition, the mixture is refluxed for 30 minutes then poured into ice (2000 g) and allowed to stand until all the ice has melted. The mixture is then extracted with methylene chloride and the organic layer is dried over magnesium sulfate and rotary evaporated. The residue is purified by flash chromatography on silica gel, eluting with methylene chloride to afford 2,3-diamino-6-nitrotoluene as an orange solid.

4-Methyl-5-nitrobenzimidazole. A mixture of 2,3-diamino-6-nitrotoluene (11.81 g), formic acid (88%, 390 mL) and 12N HCl (38 mL) is heated to reflux for 1 hour. The resulting mixture is cooled to room temperature and rotary evaporated. The residue is diluted with water (200 mL), then basified with ammonium hydroxide (28–30%). The suspension is extracted with ethyl acetate (3×200 mL). The combined extracts are dried over magnesium sulfate (MgSO$_4$) and evaporated to afford 4-methyl-5-nitrobenzimidazole as an orange solid.

1-tert-Butoxycarbonyl-4-methyl-5-nitrobenzimidazole. A suspenion of 4-methyl-5-nitrobenzimidazole (11.25 g), di-tert-butyl-dicarbonate (21.58 g), triethylamine (11.7 mL) and 4-dimethylaminopyridine (DMAP) (0.1 g) in a mixture of methanol (800 mL) and ethyl acetate (400 mL) is stirred at room temperature overnight. The mixture is rotary evaporated and the residue purified by flash chromatography on silica gel, eluting with 10% ethyl acetate in hexane. The product-containing fractions are combined and rotary evaporated to afford a white solid contaminated with a yellow oil. The solid is dissolved in methylene chloride (CH$_2$Cl$_2$) and enough hexane is added to cause precipitation. The solid is filtered and washed with 50% methylene chloride/hexane. The filtrate is rotary evaporated and the process repeated until no more clean white solid is obtained by precipitation. The combined solid fractions are dried in vacuo to afford 1-tert-butoxycarbonyl-4-methyl-5-nitrobenzimidazole as a white solid.

5-Amino-1-tert-butoxycarbonyl-4-methylbenzimidazole. To a solution of 1-tert-butoxycarbonyl-4-methyl-5-nitrobenzimidazole (8 g) in methanol (40 mL)/ethyl acetate (400 mL) is added palladium-on-carbon (Pd/C) (10%, 0.5 g) and ammonium formate (7.27g). The mixture is stirred at 50° C. for 2 hours, then filtered on Celite, with methanol wash of the solids. The filtrate is rotary evaporated and the residue partitioned between water and ethyl acetate. The organic layer is washed with saturated ammonium chloride, dried over magnesium sulfate, filtered and rotary evaporated to afford pure 5-amino-1-tert-butoxycarbonyl-4-methylbenzimidazole as an off-white solid.

1-tert-Butoxycarbonyl-4-methyl-5-benzimidazolylisothiocyanate. To a solution of di-2-pyridyl thionocarbonate (DPT) (14.3 g) and 4-dimethylaminopyridine (0.1 g) in CH$_2$Cl$_2$ (500 mL) is added dropwise over 30 minutes a solution of 5-amino-1-tert-butoxycarbonyl-4-methylbenzimidazole (7.82 g) in CH$_2$Cl$_2$ (250 mL). The mixture is stirred for 15 minutes at room temperature then rotary evaporated. The residue is purified by flash chromatography on silica gel, eluting with 10% ethyl acetate/hexane to afford 1-tert-butoxycarbonyl-4-methyl-5-benzimidazolylisothiocyanate as a white solid.

N-(1-tert-Butoxycarbonyl-4-methyl-5-benzimidazolyl)-N'-2-aminoethylthiourea. A solution of 1-tert-butoxycarbonyl-4-methyl-5-benzimidazolylisothiocyanate (7.0 g) in CH$_2$Cl$_2$ (600 mL) is added dropwise over 45 minutes to ethylenediamine (8 mL) in solution in CH$_2$Cl$_2$ (200 mL). The mixture is stirred for 3 hours at room temperature. Ether (150 mL) is added to the suspension and the mixture is stirred for 10 minutes at room temperature. The solid is filtered. The filtrate is rotary evaporated, the residue diluted with CH$_2$Cl$_2$ and reprecipitated with ether to afford a second crop. The combined solids are dried overnight in vacuo to afford N-(1-tert-butoxycarbonyl-4-methyl-5-benzimidazolyl)-N'-2-aminoethylthiourea as a white solid.

1-tert-Butoxycarbonyl-4-methyl-5-(2-imidazolinylamino)benzimidazole. A mixture of N-(1-tert-butoxycarbonyl-4-methyl-5-benzimidazolyl)-N'-2-aminoethylthiourea (2.89 g) and mercuric acetate (3.32 g) in methanol (200 mL)/chloroform (100 mL) is stirred at room temperature for 2 hours. The resulting black mixture is filtered on Celite and the filtrate rotary evaporated. The residue is purified by flash chromatography on a short pad of silica gel, eluting with 10% methanol/chloroform containing 1% ammonium hydroxide. The product-containing fractions are collected and rotary evaporated to afford 1-tert-butoxycarbonyl-4-methyl-5-(2-imidazolinylamino)benzimidazole as a white solid.

4-Methyl-5-(2-imidazolinylamino)benzimidazole dihydrobromide. To a solution of 1-tert-butoxycarbonyl-4-methyl-5-(2-imidazolinylamino)benzimidazole (2.40 g) in glacial acetic acid (50 mL) is added a solution of hydrobromic acid in glacial acetic acid (30%, 6 mL). The mixture is stirred at room temperature and gas evolution is monitored. After the gas evolution has stopped (about 1 hour), the precipitate is filtered and washed with ether. The solid is recrystallized from methanol/ether and dried in vacuo to afford 4-methyl-5-(2-imidazolinylamino)benzimidazole dihydrobromide as a pale rose solid.

EXAMPLE 2

Synthesis of 4-ethyl-5-(2-imidazolinylamino)benzimidazole dihydrobromide:

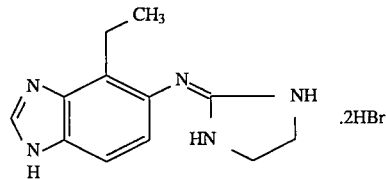

4-ethyl-5-(2-imidazolinylamino)benzimidazole dihydrobromide is made in the same manner as 4-methyl-5-(2-imidazolinylamino)benzimidazole dihydrobromide (see Example 1) except that 2-amino-3-ethyl-4-nitroaniline is used in place of 2,3-diamino-6-nitrotoluene.

EXAMPLE 3

Synthesis of 4,7-Dimethyl-5-(2-imidazolinylamino)benzimidazole sesquifumarate:

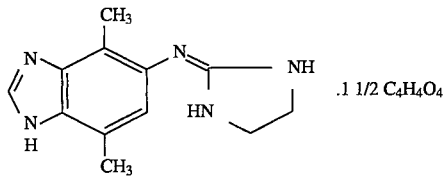

4,7-Dimethylbenzimidazole. A mixture of 2,3-diamino-p-xylene (5.1 g), formic acid (88%, 200 mL) and 12N HCl (20 mL) is heated to reflux for 3 hours. The resulting mixture is cooled to room temperature and rotary evaporated. The residue is diluted with water (100 mL), then basified with ammonium hydroxide (28–30%). The suspension is extracted with ethyl acetate (3×100 mL). The combined extracts are dried over MgSO$_4$ and rotary evaporated to afford 4,7-dimethylbenzimidazole as a yellow solid.

4,7-Dimethyl-5-nitrobenzimidazole. To a cold (ice bath) solution of 4,7-dimethylbenzimidazole (1 g) in concentrated sulfuric acid (8 mL) is added dropwise concentrated nitric acid (0.37 mL), over 50 minutes. The mixture is stirred an additional 30 minutes in the ice bath, then poured into a mixture of crushed ice (30 mL) and ammonium hydroxide (30 mL). The resulting mixture is extracted with ethyl acetate. The extract is dried over MgSO$_4$ and rotary evaporated to afford 4,7-dimethyl-5-nitrobenzimidazole as a dark tan solid.

5-Amino-4,7-dimethylbenzimidazole. To a solution of 4,7-dimethyl-5-nitrobenzimidazole (1.17 g) in methanol (150 mL) is added Pd/C (10%, 0.16 g) and ammonium formate (1.31 g). The mixture is stirred at room temperature overnight, then filtered on Celite, with methanol wash of the solids. The filtrate is rotary evaporated and the residue partitioned between water and ethyl acetate. The organic layer is washed with saturated ammonium chloride, dried over magnesium sulfate, filtered and rotary evaporated to afford 5-amino-4,7-dimethylbenzimidazole as a foamy reddish solid.

4,7-Dimethyl-5-benzimidazolylisothiocyanate. To a solution of di-2-pyridyl thionocarbonate (2.29 g) and 4-dimethylaminopyridine (0.03 g) in CH$_2$Cl$_2$ (150 mL) is added dropwise over 30 minutes a solution of 5-amino-4,7-dimethylbenzimidazole (0.816 g) in methanol (50 mL). The mixture is stirred for 3 hours at room temperature, then rotary evaporated. The residue is purified by flash chromatography on silica gel, eluting with a gradient of 50% to 80% ethyl acetate/hexane to afford 4,7-dimethyl-5-benzimidazolylisothiocyanate as a white solid.

N-(4,7-Dimethyl-5-benzimidazolyl)-N'-2-aminoethylthiourea. A solution of 4,7-dimethyl-5-benzimidazolylisothiocyanate (0.59 g) in CH$_2$Cl$_2$ (50 mL)/methanol (5 mL) is added dropwise over 20 minutes to ethylenediamine (1 mL) in solution in CH$_2$Cl$_2$ (150 mL). The mixture is stirred for 2 hours at room temperature. The resulting suspension is filtered and the solid is dried overnight in vacuo to afford N-(4,7-dimethyl-5-benzimidazolyl)-N'-2-aminoethylthiourea as a white solid.

4,7-Dimethyl-5-(2-imidazolinylamino)benzimidazole sesquifumarate. A mixture of N-(4,7-dimethyl-5-benzimidazolyl)-N'-2-aminoethylthiourea (0.77 g) and cupric acetate (0.81 g) in methanol (100 mL) is stirred at 65°–70° C. for 40 minutes. The mixture is cooled to room temperature, NaHS.xH$_2$O is added and the resulting mixture is stirred for 10 minutes at room temperature. The mixture is acidified to pH=3 with 1N HCl and filtered on Celite. The filtrate is basified to pH=9 with 50% sodium hydroxide and rotary evaporated. The syrupy residue is diluted with water (20 mL) and lyophilized. The solid residue is purified by flash chromatography on a short pad of silica gel, eluting first with 10% methanol/chloroform containing 0.1% ammonium hydroxide, then 30% methanol/chloroform containing 1% ammonium hydroxide. The product-containing fractions are collected and rotary evaporated. The residue is diluted with water (5 mL) and lyophilized to afford 4,7-dimethyl-5-(2-imidazolinylamino)benzimidazole as a yellow glassy solid. A fumarate salt is obtained by treating a solution of 4,7-dimethyl-5-(2-imidazolinylamino)benzimidazole in methanol (20 mL) with fumaric acid (0.278 g). The mixture is heated to achieve solubilization, then cooled to room temperature. The precipitate is filtered and recrystallized twice from methanol/water to afford 4,7-dimethyl-5-(2-imidazolinylamino)benzimidazole sesquifumarate.

EXAMPLE 4

Synthesis of 1,4-Dimethyl-5-(2-imidazolinylamino) benzimidazole.HOAc:

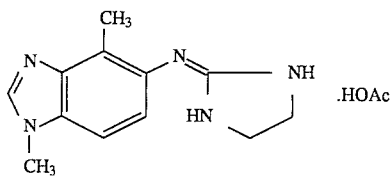

2,4-Dinitro-3-methyl-formanilide. To a solution of 2,4-dinitro-3-methylaniline (2 g) in formic acid (99%, 10 mL) heated at 55° C., is added dropwise acetic anhydride (2.5 mL), over 15 minutes. The mixture is stirred for 1 hour at 55° C. then cooled to room temperature and rotary evaporated. The residue is diluted with ethyl acetate (100 mL), washed with saturated NaHCO$_3$, dried over magnesium sulfate and rotary evaporated. The residue is purified by flash chromatography, eluting with chloroform, to afford 2,4-dinitro-3-methyl-formanilide as a white solid.

N,3-Dimethyl-2,4-dinitroaniline. To a solution of 2,4-dinitro-3-methylformanilide (1.15 g) in dry tetrahydrofuran (40 mL) is added borane-dimethyl sulfide complex (1.21 mL). The mixture is refluxed for 2 hours, then cooled in an ice bath; methanol (30 mL) is added and the stirring is maintained for 1 hour at 0° C. The mixture is acidified to pH=2 with concentrated HCl and heated to reflux for 1 hour, diluted with methanol (70 mL) and rotary evaporated. The solid residue is suspended in water (150 mL) and basified to pH=12 with concentrated NaOH. The mixture is extracted with chloroform, and the organic layer is dried over potassium carbonate and rotary evaporated. The residue is purified by flash chromatography on silica gel, eluting with 25% ethyl acetate/hexane to afford N,3-dimethyl-2,4-dinitroaniline as an orange solid.

N,3-Dimethyl-2,4-dinitroformanilide. To a solution of N,3-dimethyl-2,4-dinitroaniline (0.45 g) in formic acid (99%, 10 mL)/chloroform (4 mL) heated to 55° C., is added dropwise, acetic anhydride (1 mL), in two portions at 1 hour intervals. The mixture is stirred for 5 hours at 55° C., then cooled to room temperature, poured into 1N NaOH (50 mL) and basified to pH=12 with conc. NaOH. The mixture is extracted with methylene chloride, and the organic layer is dried over magnesium sulfate and rotary evaporated. The residue is purified by flash chromatography, eluting with chloroform, to afford N,3-dimethyl-2,4-dinitroformanilide as a white solid.

2,4-Diamino-N,3-dimethylformanilide. To a solution of N,3-dimethyl-2,4-dinitroformanilide (0.44 g) in methanol (30 mL)/ethyl acetate (10 mL) is added palladium-on-carbon (10%, 95 mg) and ammonium formate (0.93 g), and the mixture is stirred for 2 hours at room temperature. The mixture is filtered on Celite, with methanol wash of the solids, and the filtrate is rotary evaporated. The residue is partitioned between methylene chloride and water. The aqueous layer is extracted 4 times with methylene chloride. The combined extracts are dried over magnesium sulfate and rotary evaporated to afford 2,4-diamino-N,3-dimethylformanilide as a brown solid.

5-Amino-1,4-dimethylbenzimidazole. A suspension of 2,4-diamino-N,3-dimethylformanilide (0.24 g) in 2N HCl (10 mL) is heated to reflux for 1.5 hours. The mixture is diluted with water (50 mL), basified with 1N NaOH and extracted with ethyl acetate. The organic layer is dried over magnesium sulfate and rotary evaporated to afford 5-amino-1,4-dimethylbenzimidazole.

1,4-Dimethyl-5-benzimidazolylisothiocyanate. To a solution of di-2-pyridyl thionocarbonate (494 mg) and 4-dimethylaminopyridine (0.01 g) in methylene chloride (40 mL) is added dropwise over 30 minutes, a solution of 5-amino-1,4-dimethylbenzimidazole (176 mg) in methylene chloride (20 mL). The mixture is stirred for 3 hours at room temperature, then rotary evaporated. The residue is purified by flash chromatography on silica gel, eluting with 50% ethyl acetate/hexane, to afford 1,4-dimethyl-5-benzimidazolylisothiocyanate as a white solid.

1,4-Dimethyl-5-(2-imidazolinylamino)benzimidazole.HOAc. A solution of 1,4-dimethyl-5-benzimidazolylisothiocyanate (210 mg) in methylene chloride (40 mL) is added dropwise over 20 minutes to ethylenediamine (0.35 mL) in solution in methylene chloride (100 mL). The mixture is stirred for 1 hour at room temperature, then rotary evaporated. The residue is dissolved in methanol (70 mL), mercuric acetate (395 mg) is added, and the mixture is stirred at room temperature for 2 hours. The resulting black suspension is filtered on Celite with methanol wash of the solids. The filtrate is rotary evaporated, and the residue is purified by flash chromatography on silica gel, eluting with 10% methanol/chloroform containing 0.1% of ammonium hydroxide. The product-containing fractions are combined and rotary evaporated to yield 1,4-dimethyl-5-(2-imidazolinylamino)benzimidazole.HOAc.

EXAMPLE 5

Synthesis of
7-fluoro-4-methyl-5-(2-imidazolinylamino)
benzimidazole:

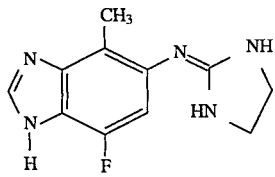

2,3-Dinitro-4-fluorotoluene. Fuming sulfuric acid (180 mL) is added dropwise to 4-fluoro-2-nitrotoluene (50.21 g) under an argon atmosphere. The internal temperature of the mixture is maintained at 0°–5° C. using an ice/sodium chloride bath. A preformed (ice bath) mixture of fuming nitric acid (30 mL) and fuming sulfuric acid (90 mL) is added dropwise to the previous solution over three hours. The reaction is then allowed to warm to room temperature. After stirring at room temperature for two hours, the mixture is poured slowly into ice and the products are extracted with methylene chloride (4×500 mL). The combined extracts are dried over magnesium sulfate, filtered and rotary evaporated. The crude product is purified by flash chromatography on silica gel, eluting with 5% ethyl acetate/hexane to afford 2,3-dinitro-4-fluorotoluene as a pale yellow solid.

4-Fluoro-7-methylbenzimidazole. A suspension of 2,3-dimethyl-4-fluorotoluene (1 g), iron powder (1.95 g) and palladium-on-carbon (10%, 150 mg) in formic acid (99%, 25 mL) is heated to reflux for 2.5 hours. The resulting mixture is filtered through Celite, with methanol wash of the solids. The filtrate is rotary evaporated and the residue partitioned between water and ethyl acetate. The organic layer is dried over magnesium sulfate, filtered and rotary evaporated to afford 4-fluoro-7-methylbenzimidazole as an off-white solid.

7-Fluoro-4-methyl-5-nitrobenzimidazole. To a cold (ice bath) solution of 4-fluoro-7-methylbenzimidazole (734 mg) in concentrated sulfuric acid (10 mL) is added dropwise concentrated nitric acid (0.22 mL) over 1 hour. The mixture is stirred an additional 15 minutes in the ice bath, then poured in a mixture of crushed ice (20 mL) and ammonium hydroxide (20 mL). The resulting mixture is extracted with ethyl acetate. The extract is dried over magnesium sulfate, filtered and rotary evaporated to afford 7-fluoro-4-methyl-5-nitrobenzimidazole as a pale yellow solid.

1-tert-Butoxycarbonyl-7-fluoro-4-methyl-5-nitrobenzimidazole. A suspension of 7-fluoro-4-methyl-5-nitrobenzimidazole (0.556 g) di-tert-butyldicarbonate (0.870 g), triethylamine (0.475 mL) and 4-dimethylaminopyridine (0.01 g)in ethyl acetate (100 mL) is stirred at room temperature overnight. The mixture is rotary evaporated and the residue purified by flash chromatography on silica gel, eluting with 10% ethyl acetate/hexane to afford 1-tert-butoxycarbonyl-7-fluoro-4-methyl-5-nitrobenzimidazole as an off-white solid.

5-Amino-1-tert-butoxycarbonyl-7-fluoro-4-methylbenzimidazole. To a solution of 1-tert-butoxycarbonyl-7-fluoro-4-methyl-5-nitrobenzimidazole (0.776 g) in methanol (100 mL)/ethyl acetate (50 mL) is added palladium-on-carbon (10%, 0.1 g) and ammonium formate (0.663 g). The mixture is stirred at room temperature for 5 hours, then filtered on Celite, with methanol wash of the solids. The filtrate is rotary evaporated and the residue partitioned between water and ethyl acetate. The organic layer is dried over magnesium sulfate, filtered and rotary evaporated. The residue is purified by flash chromatography on silica gel, eluting with 25% ethyl acetate/hexane to afford 5-amino-1-tert-butoxycarbonyl-7-fluoro-4-methylbenzimidazole as a yellow oil.

1-tert-Butoxycarbonyl-7-fluoro-4-methyl-5-benzimidazolylisothiocyanate. To a solution of di-2-pyridyl thionocarbonate (0.393 mg) and 4-dimethylaminopyridine (0.01 g) in methylene chloride (100 mL) is added dropwise over 30 minutes a solution of 5-amino-1-tert-butoxycarbonyl-7-fluoro-4-methylbenzimidazole (0.409 g) in methylene chloride (70 mL). The mixture is stirred at room temperature for 3 hours then rotary evaporated. The residue is purified by flash chromatography on silica gel, eluting with 10% ethyl acetate/hexane to afford 1-tert-butoxycarbonyl-7-fluoro-4-methyl-5-benzimidazolylisothiocyanate as a white solid.

N-(1-tert-Butoxycarbonyl-7-fluoro-4-methyl-5-benzimidazolyl)-N'-2-aminoethylthiourea. A solution of 1-tert-butoxycarbonyl-7-fluoro-4-methyl-5-benzimidazolylisothiocyanate (0.42 g) in methylene chloride (50 mL) is added dropwise over 15 minutes to 1,2-ethylenediamine (0.45 mL) in solution in methylene chloride (100 mL). The mixture is stirred for 10 minutes at room temperature, then rotary evaporated. The residue is triturated for 30 minutes with ether (100 mL). The resulting white suspension is filtered and the solid is dried in vacuo overnight.

7-Fluoro-4-methyl-5-(2-imidazolinylamino)benzimidazole. A mixture of N-(1-tert-butoxycarbonyl-7-fluoro-4-methyl-5-benzimidazolyl)-N'-2-aminoethylthio-urea (0.5 g) and mercuric acetate (0.52 g) in methanol (150 mL) is stirred at room temperature for 1 hour. The resulting black mixture is filtered on Celite with methanol wash of the solids. The filtrate is rotary evaporated and the residue filtered through a short pad of silica gel, eluting 25% methanol in chloroform containing 1% of ammonium hydroxide. The product-containing fractions are rotary evaporated, the residue diluted with water (15 mL), filtered through a plug of glass wool and lyophilized to afford 7-fluoro-4-methyl-5-(2-imidazolinylamino)benzimidazole as a pale yellow solid.

Compositions

Another aspect of the subject invention is compositions which comprise a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgement. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.0001% to about 99% by weight of the subject compound, more preferably from about 0.01% to about 90%; also preferably from about 10% to about 50%, also preferably from about 5% to about 10%, also preferably from about 1% to about 5%, and also preferably from about 0.1% to about 1%.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

The preferred mode of administering the subject compounds is perorally. The preferred unit dosage form is therefore tablets, capsules, lozenges, chewable tablets, and the like. Such unit dosage forms comprise a safe and effective amount of the subject compound, which is preferably from about 0.01 mg to about 200 mg, more preferably from about 0.1 mg to about 50 mg, more preferably still from about 0.5 mg to about 25 mg, also preferably from about 1 mg to about 10 mg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A preferred mode of administering the subject compounds is topically to the site where activity is desired: intranasal doses for nasal decongestion, inhalants for asthma, eye drops, gels and creams for ocular disorders, and peroral doses for gastrointestinal disorders.

Preferred compositions of the subject invention include aqueous solutions comprising a safe and effective amount of a subject compound intended for topical intranasal administration. Such compositions preferably comprise from about 0.001% to about 5% of a subject compound, more preferably from about 0.01% to about 0.5%. Such compositions also typically include safe and effective amounts of preservatives, such as benzalkonium chloride and thimerosal; buffers such as phosphate and acetate; tonicity agents such as sodium chloride; antioxidants such as ascorbic acid; aromatic agents; and acids and bases to adjust the pH of these aqueous compositions as needed.

Preferred compositions of the subject invention include aqueous solutions, suspensions, and dry powders comprising a safe and effective amount of a subject compound intended for atomization and topical inhalation administration. Such compositions preferably comprise from about 0.1% to about 50% of a subject compound, more preferably from about 1% to about 20%. Such compositions are typically contained in a container with attached atomizing means. Such compositions also typically include propellants such as chlorofluorocarbons 12/11 and 12/114; solvents such as water, glycerol and ethanol; stabilizers such as ascorbic acid, sodium metabisulfite; preservatives such as cetylpyridinium chloride and benzalkonium chloride; tonicity adjustors such as sodium chloride; and flavoring agents such as sodium saccharin.

Preferred compositions of the subject invention include aqueous solutions comprising a safe and effective amount of a subject compound intended for topical intraocular administration. Such compositions preferably comprise from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases may be used to adjust the pH of these formulations as needed.

Preferred compositions of the subject invention include solids, such as tablets and capsules, and liquids, such as solutions, suspensions and emulsions (preferably in soft gelatin capsules), comprising a safe and effective amount of a subject compound intended for topical administration to the gastrointestinal tract by peroral administration. Such compositions preferably comprise from about 0.01 mg to about 100 mg per dose, more preferably from about 0.1 mg to about 5 mg per dose. Such compositions can be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Compositions of the subject invention may optionally include other drug actives. Non-limiting examples of drug actives which may be incorporated in these compositions, include:

Antihistamines, including;

Hydroxyzine preferably at a dosage range of from about 25 to about 400 mg; Doxylamine, preferably at a dosage range of from about 3 to about 75 mg; Pyrilamine, preferably at a dosage range of from about 6.25 to about 200 mg; Chlorpheniramine, preferably at a dosage range of from about 1 to about 24 mg; Phenindamine, preferably at a dosage range of from about 6.25 to about 150 mg; Dexchlorpheniramine, preferably at a dosage range of from about 0.5 to about 12 mg; Dexbrompheniramine, preferably at a dosage range of from about 0.5 to about 12 mg; Clemastine, preferably at a dosage range of from about 1 to about 9 mg; Diphenhydramine, preferably at a dosage range of from about 6.25 to about 300 mg; Azelastine, preferably at a dosage range of from about 140 to about 1,680 ug (when dosed intranasally); 1 to about 8 mg (when dosed orally); Acrivastine, preferably at a dosage range of from about 1 to about 24 mg; Levocarbastine (which can be dosed as an intranasal or ocular medicament), preferably at a dosage range of from about 100 to about 800 ug; Mequitazine, preferably at a dosage range of from about 5 to about 20 mg; Astemizole, preferably at a dosage range of from about 5 to about 20 mg; Ebastine;Loratadine, preferably at a dosage range of from about 5 to about 40 mg; Cetirizine, preferably at a dosage range of from about 5 to about 20 mg; Terfenadine, preferably at a dosage range of from about 30 to about 480 mg; Terfenadine metabolites; Promethazine, preferably at a dosage range of from about 6.25 to about 50 mg; Dimenhydrinate, preferably at a dosage range of from about 12.5 to about 400 mg; Meclizine, preferably at a dosage range of from about 6.25 to about 50 mg; Tripelennamine, preferably at a dosage range of from about 6.25 to about 300 mg; Carbinoxamine, preferably at a dosage range of from about 0.5 to about 16 mg; Cyproheptadine, preferably at a dosage range of from about 2 to about 20 mg; Azatadine, preferably at a dosage range of from about 0.25 to about 2 mg; Brompheniramine, preferably at a dosage range of from about 1 to about 24 mg; Triprolidine, preferably at a dosage range of from about 0.25 to about 10 mg; Cyclizine, preferably at a dosage range of from about 12.5 to about 200 mg; Thonzylamine, preferably at a dosage range of from about 12.5 to about 600 mg; Pheniramine, preferably at a dosage range of from about 3 to about 75 mg; Cyclizine, preferably at a dosage range of from about 12.5 to about 200 mg and others;

Antitussives, including;

Codeine, preferably at a dosage range of from about 2.5 to about 120 mg; Hydrocodone, preferably at a dosage range of from about 2.5 to about 40 mg; Dextromethorphan, preferably at a dosage range of from about 2.5 to about 120 mg; Noscapine, preferably at a dosage range of from about 3 to about 180 mg; Benzonatate, preferably at a dosage range of from about 100 to about 600 mg; Diphenhydramine, preferably at a dosage range of from about 12.5 to about 150 mg; Chlophedianol, preferably at a dosage range of from about 12.5 to about 100 mg; Clobutinol, preferably at a dosage range of from about 20 to about 240 mg; Fominoben, preferably at a dosage range of from about 80 to about 480 mg; Glaucine; Pholcodine, preferably at a dosage range of from about 1 to about 40 mg; Zipeprol, preferably at a dosage range of from about 75 to about 300 mg; Hydromorphone, preferably at a dosage range of from about 0.5 to about 8 mg; Carbetapentane, preferably at a dosage range of from about 15 to about 240 mg; Caramiphen, Levopropoxyphene, preferably at a dosage range of from about 25 to about 200 mg and others;

Antiinflammatories, preferably Non-Steroidal Anti-inflammatories, (NSAIDS) including;

Ibuprofen, preferably at a dosage range of from about 50 to about 3,200 mg; Naproxen, preferably at a dosage range of from about 62.5 to about 1,500 mg; Sodium naproxen, preferably at a dosage range of from about 110 to about 1,650 mg; Ketoprofen, preferably at a dosage range of from about 25 to about 300 mg; Indoprofen, Indomethacin, preferably at a dosage range of from about 25 to about 200mg; Sulindac, preferably at a dosage range of from about 75 to about 400 mg; Diflunisal, preferably at a dosage range of from about 125 to about 1,500 mg; Ketorolac, preferably at a dosage range of from about 10 to about 120 mg; Piroxicam, preferably at a dosage range of from about 10 to about 40 mg; Aspirin, preferably at a dosage range of from about 80 to about 4,000 mg; Meclofenamate, preferably at a dosage range of from about 25 to about 400 mg; Benzydamine, preferably at a dosage range of from about 25 to about 200 mg; Carprofen, preferably at a dosage range of from about 75 to about 300 mg; Diclofenac, preferably at a dosage range of from about 25 to about 200 mg; Etodolac, preferably at a dosage range of from about 200 to about 1,200 mg; Fenbufen, preferably at a dosage range of from about 300 to about 900 mg; Fenoprofen, preferably at a dosage range of from about 200 to about 3,200 mg; Flurbiprofen, preferably at a dosage range of from about 50 to about 300 mg; Mefenamic acid, preferably at a dosage range of from about 250 to about 1,500 mg; Nabumetone, preferably at a dosage range of from about 250 to about 2,000 mg; Phenylbutazone, preferably at a dosage range of from about 100 to about 400 mg; Pirprofen, preferably at a dosage range of from about 100 to about 800 mg; Tolmetin, preferably at a dosage range of from about 200 to about 1,800 mg and others;

Analgesics, including;

Acetaminophen, preferably at a dosage range of from about 80 to about 4,000 mg; and others:

Expectorants/Mucolytics, including;

Guaifenesin, preferably at a dosage range of from about 50 to about 2,400mg; N-Acetylcysteine, preferably at a dosage range of from about 100 to about 600 mg; Ambroxol, preferably at a dosage range of from about 15 to about 120 mg; Bromhexine, preferably at a dosage range of from about 4 to about 64 mg; Terpin hydrate, preferably at a dosage range of from about 100 to about 1,200 mg; Potassium iodide, preferably at a dosage range of from about 50 to about 250 mg and others;

Atropinics, preferably intranasally or orally administered atropinics, including;

Ipratroprium (preferably intranasally), preferably at a dosage range of from about 42 to about 252 ug; Atropine sulfate (preferably oral), preferably at a dosage range of from about 10 to about 1,000 ug; Belladonna (preferably as an extract), preferably at a dosage range of from about 15 to about 45 mg equivalents; Scopolamine, preferably at a dosage range of from about 400 to about 3,200 ug; Scopolamine methobromide, preferably at a dosage range of from about 2.5 to about 20 mg; Homatropine methobromide, preferably at a dosage range of from about 2.5 to about 40 mg; Hyoscyamine (preferably oral), preferably at a dosage range of from about 125 to about 1,000 ug; Isopropramide (preferably oral), preferably at a dosage range of from about 5 to about 20 mg; Orphenadrine (preferably oral), preferably at a dosage range of from about 50 to about 400 mg; Benzalkonium chloride (preferably intranasally) preferably a 0.005 to about 0.1% solution and others;

Mast Cell Stabilizers, preferably intranasally, or orally administered mast cell stabilizers, including;

Cromalyn, preferably at a dosage range of from about 10 to about 60 mg; Nedocromil, preferably at a dosage range of from about 10 to about 60 mg; Oxatamide, preferably at a dosage range of from about 15 to about 120 mg; Ketotifen, preferably at a dosage range of from about 1 to about 4 mg; Lodoxamide, preferably at a dosage range of from about 100 to about 3,000 ug and others;

LT Antagonists, including Zileuton and others;

Methylxanthines, including;

Caffeine, preferably at a dosage range of from about about 65 to about 600 mg; Theophyllene, preferably at a dosage range of from about 25 to about 1,200 mg; Enprofylline; Pentoxifylline, preferably at a dosage range of from about 400 to about 3,600 mg; Aminophylline, preferably at a dosage range of from about 50 to about 800 mg; Dyphylline, preferably at a dosage range of from about 200 to about 1,600 mg and others;

Antioxidants or radical inhibitors, including;

Ascorbic acid, preferably at a dosage range of from about 50 to about 10,000 mg; Tocopherol, preferably at a dosage range of from about 50 to about 2,000 mg; Ethanol, preferably at a dosage range of from about 500 to about 10,000 mg and others;

Steroids, preferably intranasally administered steroids, including:

Beclomethasone, preferably at a dosage range of from about 84 to about 336 ug; Fluticasone, preferably at a dosage range of from about 50 to about 400 ug; Budesonide, preferably at a dosage range of from about 64 to about 256 ug; Mometasone; Triamcinolone, preferably at a dosage range of from about 110 to about 440 ug; Dexamethasone, preferably at a dosage range of from about 168 to about 1,008 ug; Flunisolide, preferably at a dosage range of from about 50 to about 300 ug; Prednisone (preferably oral), preferably at a dosage range of from about 5 to about 60 mg; Hydrocortisone (preferably oral), preferably at a dosage range of from about 20 to about 300 mg and others;

Bronchodilators, preferably for inhalation, including;

Albuterol, preferably at a dosage range of from about 90 to about 1,080 ug; 2 to about 16 mg (if dosed orally); Epinephrine, preferably at a dosage range of from about 220 to about 1,320 ug; Ephedrine, preferably at a dosage range of from about 15 to about 240 mg (if dosed orally); 250 to about 1,000 ug (if dosed intranasally); Metaproterenol, preferably at a dosage range of from about 65 to about 780 ug or 10 to about 80 mg if dosed orally; Terbutaline, preferably at a dosage range of from about 200 to about 2,400 ug; 2.5 to about 20 mg if dosed orally; Isoetharine, preferably at a dosage range of from about 340 to about 1,360 ug; Pirbuterol, preferably at a dosage range of from about 200 to about 2,400 ug; Bitolterol, preferably at a dosage range of from about 370 to about 2,220 ug; Fenoterol, preferably at a dosage range of from about 100 to about 1,200 ug; 2.5 to about 20 mg (if dosed orally); Rimeterol, preferably at a dosage range of from about 200 to about 1,600 ug; Ipratroprium, preferably at a dosage range of from about 18 to about 216 ug (inhalation) and others; and Antivirals, including;

Amantadine, preferably at a dosage range of from about 50 to about 200 mg; Rimantadine, preferably at a dosage range of from about 50 to about 200 mg; Enviroxime; Nonoxinols, preferably at a dosage range of from about 2 to about 20 mg (preferably an intranasal form); Acyclovir, preferably at a dosage range of from about 200 to about 2,000 mg (oral); 1 to about 10 mg (preferably an intranasal form); Alpha-lnterferon, preferably at a dosage range of from about 3 to about 36 MIU; Beta-Interferon, preferably at a dosage range of from about 3 to about 36 MIU and others;

Ocular Drug actives:

acetylcholinesterase inhibitors, e.g., echothiophate from about 0.03% to about 0.25% in topical solution and others; and Gastrointestinal actives:

antidiarrheals, e.g., Ioperamide from about 0.1 mg to about 1.0 mg per dose, and bismuth subsalicylate from about 25 mg to about 300 mg per dose and others.

Of course, clearly contemplated and included in the description above are the acid or base addition salts, esters, metabolites, steoisomers and enatiomers of these preferred actives, as well as analogues to these actives that are safe and effective. It is also recognized that an active may be useful for more than one of the above uses, and these uses are clearly contemplated as well. This overlap is recognized in the art and adjusting dosages and the like to fit the indication is well within the perview of the skilled medical practitioner.

Methods

Another aspect of the subject invention involves methods for preventing or treating nasal congestion by administering a safe and effective amount of a subject compound to a human or lower animal experiencing or at risk of experiencing nasal congestion. Such nasal congestion may be associated with human diseases or disorders which include, but are not limited to, seasonal allergic rhinitis, acute upper respiratory viral infections, sinusitis, perennial rhinitis, and vasomotor rhinitis. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily. Such doses and frequencies are also preferred for treating other respiratory conditions, such as otitis media, cough, COPD and asthma.

Another aspect of the subject invention involves methods for preventing or treating glaucoma by administering a safe and effective amount of a subject compound to a human or lower animal experiencing or at risk of experiencing glaucoma. Each administration of a dose of the subject compound preferably administers a dose within the range of from about 0.01 μg/kg to about 10 mg/kg of a compound, more preferably from about 0.001 mg/kg to about 1 mg/kg, more preferably still from about 0.01 mg/kg to about 0.1 mg/kg. Intraocular administration of such doses is preferred. The frequency of administration of a subject compound according to the subject invention is preferably from about once to about six times daily, more preferably from about 2 times to about 4 times daily.

Another aspect of the subject invention involves methods for preventing or treating functional bowel disorders, such as diarrhea, by administering a safe and effective amount of a subject compound to a human or lower animal experiencing or at risk of experiencing diarrhea. Each administration of a dose of the subject compound preferably administers a dose within the range of from about 0.001 mg/kg to about 10 mg/kg of a compound, more preferably from about 0.01 mg/kg to about 5 mg/kg, more preferably still from about 0.1 mg/kg to about 1 mg/kg. Peroral administration of such doses is preferred. The frequency of administration of a subject compound according to the subject invention is preferably from about once to about six times daily, more preferably from about 2 times to about 4 times daily.

Composition and Method Examples

The following non-limiting examples illustrate the compositions and methods of use of the subject invention.

EXAMPLE A

Oral Table Composition

| Ingredient | Amount per tablet (mg) |
| --- | --- |
| Subject Compound 4 | 20.0 |
| Microcrystalline cellulose (Avicel PH 102 ®) | 80.0 |
| Dicalcium phosphate | 96.0 |
| Pyrogenic silica (Cab-O-Sil ®) | 1.0 |
| Magnesium stearate | 3.0 |
| Total = | 200.0 |

One tablet is swallowed by a patient with nasal congestion. The congestion is substantially diminished.

EXAMPLE B

Chewable Tablet Composition

| Ingredient | Amount per tablet (mg) |
| --- | --- |
| Subject Compound 1 | 15.0 |
| Mannitol | 255.6 |
| Microcrystalline cellulose (Avicel PH 101 ®) | 100.8 |
| Dextrinized sucrose (Di-Pac ®) | 199.5 |
| Imitation orange flavor | 4.2 |
| Sodium saccharin | 1.2 |
| Stearic acid | 15.0 |
| Magnesium stearate | 3.0 |
| FD&C Yellow #6 dye | 3.0 |
| Pyrogenic silica (Cab-O-Sil ®) | 2.7 |
| Total = | 600.0 |

One tablet is chewed and swallowed by a patient with nasal congestion. The congestion is substantially reduced.

EXAMPLE C

Sublingual Tablet Composition

| Ingredient | Amount per tablet (mg) |
| --- | --- |
| Subject Compound 5 | 2.00 |
| Mannitol | 2.00 |
| Microcrystalline cellulose (Avicel PH 101 ®) | 29.00 |
| Mint flavorants | 0.25 |
| Sodium saccharin | 0.08 |
| Total = | 33.33 |

One tablet is placed under the tongue of a patient with nasal congestion and allowed to dissolve. The congestion is rapidly and substantially diminished.

EXAMPLE D

Intranasal Solution Composition

| Ingredient | Composition (% w/v) |
| --- | --- |
| Subject Compound 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

One-tenth of a mL of the composition is sprayed from a pump actuator into each nostril of a patient with nasal congestion. The congestion is substantially diminished.

EXAMPLE E

Intranasal Gel Composition

| Ingredient | Composition (% w/v) |
| --- | --- |
| Subject Compound 1 | 0.10 |
| Benzalkonium chloride | 0.02 |
| Thimerosal | 0.002 |
| Hydroxypropyl methylcellulose (Metolose 65SH4000 ®) | 1.00 |
| Aromatics | 0.06 |
| Sodium chloride (0.65%) | q.s. |
| Total = | 100.00 |

One-fifth of a mL of the composition is applied as drops from a dropper into each nostril of a patient with nasal congestion. The congestion is substantially reduced.

EXAMPLE F

Inhalation Aerosol Composition

| Ingredient | Composition (% w/v) |
| --- | --- |
| Subject Compound 2 | 5.0 |
| Alcohol | 33.0 |
| Ascorbic acid | 0.1 |
| Menthol | 0.1 |

-continued

| Ingredient | Composition (% w/v) |
|---|---|
| Sodium Saccharin | 0.2 |
| Propellant (F12, F114) | q.s. |
| Total = | 100.0 |

Two-puffs of the aerosol composition is inhaled from a metered-dose inhaler by a patient with asthma. The asthmatic condition is effectively relieved.

EXAMPLE G

Topical Ophthalmic Composition

| Ingredient | Composition (% w/v) |
|---|---|
| Subject Compound 5 | 0.10 |
| Benzalkonium chloride | 0.01 |
| EDTA | 0.05 |
| Hydroxyethylcellulose (Natrosol M ®) | 0.50 |
| Sodium metabisulfite | 0.10 |
| Sodium chloride (0.9%) | q.s. |
| Total = | 100.0 |

One-tenth of a mL of the composition is administered directly into each eye of a patient with glaucoma. The intraocular pressure is substantially reduced.

EXAMPLE H

Oral Liquid Composition

| Ingredient | Amount/15 mL Dose |
|---|---|
| Subject Compound 4 | 15 mg |
| Chlorpheniramine maleate | 4 mg |
| Propylene glycol | 1.8 g |
| Ethanol (95%) | 1.5 mL |
| Methanol | 12.5 mg |
| Eucalyptus oil | 7.55 mg |
| Flavorants | 0.05 mL |
| Sucrose | 7.65 g |
| Carboxymethylcellulose (CMC) | 7.5 mg |
| Microcrystalline cellulose and Sodium CMC (Avicel RC 591 ®) | 187.5 mg |
| Polysorbate 80 | 3.0 mg |
| Glycerin | 300 mg |
| Sorbitol | 300 mg |
| FD&C Red #40 dye | 3 mg |
| Sodium saccharin | 22.5 mg |
| Sodium phosphate monobasic | 44 mg |
| Sodium citrate monohydrate | 28 mg |
| Purified Water | q.s. |
| Total = | 15 mL |

One 15 mL dose of the liquid composition is swallowed by a patient with nasal congestion and runny nose due to allergic rhinitis. The congestion and runny nose are effectively reduced.

EXAMPLE J

Oral Liquid Composition

| Ingredient | Amount/15 mL Dose |
|---|---|
| Subject Compound 2 | 30 mg |
| Sucrose | 8.16 g |
| Glycerin | 300 mg |
| Sorbitol | 300 mg |
| Methylparaben | 19.5 mg |
| Propylparaben | 4.5 mg |
| Menthol | 22.5 mg |
| Eucalyptus oil | 7.5 mg |
| Flavorants | 0.07 mL |
| FD&C Red #40 dye | 3.0 mg |
| Sodium saccharin | 30 mg |
| Purified water | q.s. |
| Total = | 15 mL |

One 15 mL dose of the alcohol-free liquid medication is swallowed by a patient with nasal congestion. The congestion is substantially diminished.

EXAMPLE K

For the relief of nasal congestion due to the common cold, hay fever, or other upper respiratory allergies, or associated with sinusitis; relieves runny nose, sneezing, and itchy watery eyes as may occur in allergic rhinitis. Restores freer breathing through the nose. Adults 12 and over take one tablet every four hours.

|  | mg/tablet |
|---|---|
| chlorpheniramine maleate, USP | 4 mg |
| Subject Compound 1 | 4 |
| microcrystalline cellulose, NF | 130 |
| starch 1500, NF | 100 |
| magnesium stearate, USP | 2 |
| total | 240 mg |

EXAMPLE L

For the relief of symptoms associated with allergic rhinitis such as sneezing, rhinorrhea, and nasal congestion. Adults 12 and over take one tablet every twelve hours.

|  | mg/tablet |
|---|---|
| loratadine | 5 mg |
| Subject Compound 2 | 12 |
| hydroxypropyl methylcellulose, USP | 12 |
| magnesium stearate, USP | 2 |
| lactose anhydrous, USP | 200 |
| total | 231 mg |

EXAMPLE M

For relief of symptoms associated with the common cold, sinusitis, or flu including nasal congestion, headache, fever, body aches, and pains. Adults 12 and over take two caplets every twelve hours.

|  | mg/caplet |
|---|---|
| naproxen sodium anhydrous, USP | 220 mg |
| Subject Compound 3 | 6 |
| hydroxypropyl methylcellulose, USP | 6 |
| magnesium stearate, USP | 2 |
| povidone K-30, USP | 10 |
| talc, USP | 12 |
| microcrystalline cellulose, NF | 44 |
| total | 300 mg |

EXAMPLE N

For relief of nasal/sinus congestion and pressure, sinus headache pain associated with sinusitis, hay fever, upper respiratory allergies, or the common cold. Adults 12 and over take one tablet every six hours.

|  | mg/tablet |
|---|---|
| acetaminophen, USP | 500 mg |
| Subject Compound 4 | 6 |
| hydroxypropyl methylcellulose, USP | 6 |
| silicon dioxide, colloidal, NF | 30 |
| pregelatinized starch, NF | 50 |
| magnesium stearate, USP | 4 |
| total | 596 mg |

EXAMPLE N

For the relief of symptoms associated with allergic rhinitis such as sneezing, rhinorrhea, nasal congestion, sinus pain, and headache. Adults 12 and over take two caplets every twelve hours.

|  | mg/caplet |
|---|---|
| naproxen sodium anhydrous, USP | 220 mg |
| loratadine | 2.5 |
| Subject Compound 5 | 6 |
| hydroxypropyl methylcellulose, USP | 6 |
| magnesium stearate, USP | 2 |
| povidone K-30, USP | 10.5 |
| talc, USP | 12 |
| microcrystalline cellulose, NF | 44 |
| total | 303 mg |

EXAMPLE O

For the relief of symptoms due to the common cold, flu, hay fever, or other upper respiratory allergies, or associated with sinusitis; relieves runny nose, sneezing, and itchy watery eyes as may occur in allergic rhinitis. Relieves headache, fever, body aches, and pains. Restores freer breathing through the nose. Adults 12 and over take two tablets every twelve hours.

|  | mg/tablet |
|---|---|
| naproxen sodium anhydrous, USP | 220 mg |
| chlorpheniramine maleate, USP | 6 |
| Subject Compound 1 | 6 |
| hydroxypropyl methylcellulose, USP | 12 |
| magnesium stearate, USP | 2 |
| povidone K-30, USP | 10 |
| talc, USP | 12 |
| microcrystalline cellulose, NF | 44 |
| total | 312 mg |

EXAMPLE P

For the relief of symptoms associated with allergic rhinitis such as sneezing, rhinorrhea, nasal congestion, sinus pain, and headache. Adults 12 and over take two tablets every six hours.

|  | mg/tablet |
|---|---|
| acetaminophen, USP | 500 mg |
| loratadine | 1.3 |
| Subject Compound 5 | 3 |
| hydroxypropyl methylcellulose, USP | 3 |
| silicon dioxide, colloidal, NF | 30 |
| pregelatinized starch, NF | 50 |
| magnesium stearate, USP | 2.7 |
| total | 590 mg |

EXAMPLE Q

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

|  | mg/fl oz |
|---|---|
| acetaminophen, USP | 1000 mg |
| doxylamine succinate, USP | 12.5 |
| dextromethorphan hydrobromide, USP | 30 |
| Subject Compound 2 | 6 |
| Dow XYS-40010.00 resin | 3 |
| high fructose corn syrup | 16000 |
| polyethylene glycol, NF | 3000 |
| propylene glycol, USP | 3000 |
| alcohol, USP | 2500 |
| sodium citrate dihydrate, USP | 150 |
| citric acid, anhydrous, USP | 50 |
| saccharin sodium, USP | 20 |
| flavor | 3.5 |
| purified water, USP | 3500 |
| total | 29275 mg |

EXAMPLE R

For the relief of minor aches, pains, headache, muscular aches, sore throat pain, and fever associated with a cold or flu. Relieves nasal congestion, cough due to minor throat and bronchial irritations, runny nose, and sneezing associated with the common cold. Adults 12 and over take one fluid ounce every six hours.

|  | mg/fl oz |
|---|---|
| naproxen sodium anhydrous, USP | 220 mg |
| doxylamine succinate, USP | 12.5 |

-continued

|  | mg/fl oz |
|---|---|
| dextromethorphan hydrobromide, USP | 30 |
| Subject Compound 1 | 6 |
| Dow XYS-40010.00 resin | 3 |
| high fructose corn syrup | 16000 |
| polyethylene glycol, NF | 3000 |
| propylene glycol, USP | 3000 |
| alcohol, USP | 2500 |
| sodium citrate dihydrate, USP | 150 |
| citric acid, anhydrous, USP | 50 |
| saccharin sodium, USP | 20 |
| flavor | 3.5 |
| purified water, USP | 3800 |
| total | 28795 mg |

Other examples of combination actives are contemplated. Examples of medicaments which can be combined with the primary active are included in U.S. Pat. No. 4,552,899 to Sunshine, et al., hereby incorporated by reference. All other references referred to throughout this specification are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A pharmaceutical composition comprising the compound having the following structure:

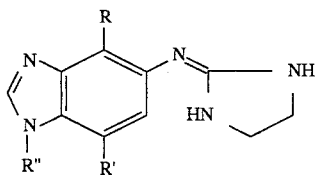

wherein:

(a) R is unsubstituted alkanyl or alkenyl having from 1 to about 3 carbon atoms;

(b) R' is selected from the group consisting of hydrogen; unsubstituted alkanyl or alkenyl having from 1 to about 3 carbon atoms; unsubstituted alkylthio or alkoxy having from 1 to about 3 carbon atoms; hydroxy; thiol; cyano; and halo;

(c) R" is selected from the group consisting of hydrogen, methyl, ethyl and i-propyl;

and one or more actives chosen from the group consisting of an antitussive, mast cell stabilizer, LT antagonist, expectorant/muycolytic, antioxidant or radical inhibitor, steroid, bronchodilator, antiviral, analgesic, antiinflammatory, gastrointestinal and ocular active.

2. A pharmaceutical composition according to claim 1 further comprising an analgesic.

3. A pharmaceutical composition according to claim 1 further comprising an antiinflammatory.

4. A pharmaceutical composition according to claim 1 further comprising an antihistamine.

5. A pharmaceutical composition according to claim 1 further comprising an muycolytic/expectorant.

6. A pharmaceutical composition according to claim 1 further comprising an antitussive.

7. A pharmaceutical composition according to claim 1 further comprising a mast cell stabilizer.

8. A pharmaceutical composition according to claim 1 further comprising a LT antagonist.

9. A pharmaceutical composition according to claim 1 further comprising an antioxidant or radical inhibitor.

10. A pharmaceutical composition according to claim 1 further comprising asteroid.

11. A pharmaceutical composition according to claim 1 further comprising a bronchodilator.

12. A pharmaceutical composition according to claim 1 further comprising an antitussive.

13. A pharmaceutical composition according to claim 1 further comprising an antiviral.

14. A pharmaceutical composition according to claim 1 further comprising an ocular drug.

15. A pharmaceutical composition according to claim 15 further comprising a gastrointestinal active.

* * * * *